United States Patent [19]

Falck-Pedersen

[11] Patent Number: 5,849,561
[45] Date of Patent: Dec. 15, 1998

[54] METHOD FOR THE PRODUCTION OF NON-GROUP C ADENOVIRAL VECTORS

[75] Inventor: Erik S. Falck-Pedersen, Dobbs Ferry, N.Y.

[73] Assignee: Cornell Research Foundation, Inc., Ithaca, N.Y.

[21] Appl. No.: 861,773

[22] Filed: May 22, 1997

[51] Int. Cl.[6] ........................................................ C12N 7/01
[52] U.S. Cl. ................................................................ 435/235.1
[58] Field of Search .......................................... 435/235.1

[56] References Cited

U.S. PATENT DOCUMENTS

| 4,920,209 | 4/1990 | Davis et al. | 435/235.1 |
| 5,543,328 | 8/1996 | McCelland et al. | 435/320.1 |

FOREIGN PATENT DOCUMENTS

| 0 638 316 | 2/1995 | European Pat. Off. |
| WO 94/12649 | 9/1994 | WIPO . |
| WO 94/28152 | 12/1994 | WIPO . |
| WO 96/09399 | 3/1996 | WIPO . |
| WO 97/12986 | 4/1997 | WIPO . |

OTHER PUBLICATIONS

Abrahamsen et al., *J. Virol.,* vol. 71, 1997, pp. 8946–8951, 1997.
Chengalvala et al., *Vaccine,* 9, 485–490 (1991).
Chengalvala et al., *J. Gen. Virol.,* 75, 125–131 (1994).
Horwitz, "Adenoviridae and Their Replication," in *Fundamental Virology* (Fields et al., eds., Raven Press Ltd., New York, NY, 2d ed., 1991) pp. 771–813.
Lindley et al., *Gene,* 138 165–170 (1994).
Straus, "Adenovirus Infections in Humans," in *Adenoviruses* (Plenum Press, New York, NY 1984), pp. 451–496.
Mastrangeli et al., *J. Clinical Investigation,* 91, 225–234 (1993).
Kremer et al, "Adenovirus and adeno–associated virus mediated gene transfer," British Medical Bulletin, vol. 51, No. 1, pp. 31–44.
Jolly, Douglas, "Viral Vector systems for Gene Therapy," Cancer Gene Therapy, vol. 1, No. 1, pp. 51–64.
Berkner, K.L., "Expression of Heterologous Sequences in Adenoviral Vectors," Current Topics in Microbiology and Immunology, vol. 158 pp. 39–66.
Crystal, Ronald G., "The Gene as the Drug, Nature Medicine," vol. 1, No. 1, pp. 15–17.
Orkin et al., "Report and recommendation of the panel to assess the NIH investment in research on gene therapy," Distributed by the NIH, Dec. 7, 1995.
Gall et al., *J. Virology,* 20, 2116–2123 (1996).

*Primary Examiner*—James Ketter
*Attorney, Agent, or Firm*—Leydig, Voit & Mayer, Ltd.

[57] ABSTRACT

A method of producing a replication deficient adenovirus comprising a passenger gene and a deficiency in an essential gene function of the E1 region of an adenovirus comprising producing the adenovirus in a cell that provides in trans gene functions of the E1 and E4 regions of one or more adenoviruses not belonging to the same serogroup as the replication deficient adenovirus.

14 Claims, No Drawings

METHOD FOR THE PRODUCTION OF NON-GROUP C ADENOVIRAL VECTORS

TECHNICAL FIELD OF THE INVENTION

The present invention relates to the production of adenoviral gene transfer vectors which comprise a passenger gene for expression within a cell.

BACKGROUND OF THE INVENTION

During the winter and spring of 1952–1953, Rowe and his colleagues at the National Institutes of Health (NIH) obtained and placed in tissue culture adenoids that had been surgically removed from young children in the Washington, D.C. area (Rowe et al., *Proc. Soc. Exp. Biol. Med.*, 84, 570–573 (1953)). After periods of several weeks, many of the cultures began to show progressive degeneration characterized by destruction of epithelial cells. This cytopathic effect could be serially transmitted by filtered culture fluids to established tissue cultures of human cell lines. The cytopathic agent was called the "adenoid degenerating" (Ad) agent. The name "adenovirus" eventually became common for these agents. The discovery of many prototype strains of adenovirus, some of which caused respiratory illnesses, followed these initial discoveries (Rowe et al., supra; Dingle et al., *Am. Rev. Respir. Dis.*, 97, 1–65 (1968); Horwitz, "Adenoviridae and Their Replication," in *Fundamental Virology* (Fields et al., eds., Raven Press Ltd., New York, N.Y., 2d ed., 1991), pp. 771–813).

All adenoviruses are morphologically and structurally similar. These viruses are non-enveloped, regular icosahedrons, 65–80 nm in diameter, consisting of an external capsid and an internal core. The capsid is composed of 20 triangular surfaces or facets and 12 vertices (Horne et al., *J. Mol. Biol.*, 1, 84–86 (1959)). The facets are comprised of hexons, and the vertices are comprised of pentons. A fiber projects from each of the vertices. In addition to the hexons, pentons, and fibers, there are eight minor structural polypeptides, the exact positions of the majority of which are unclear.

The viral core contains a linear, double-stranded DNA molecule with inverted terminal repeats (ITRs), which have been noted to vary in length from 103 bp to 163 bp in different isolates (Garon et al., *Proc. Natl. Acad. Sci. USA*, 69, 2391–2394 (1972); Wolfson et al., *Proc. Natl. Acad. Sci. USA*, 69, 3054–3057 (1972); Arrand et al., *J. Mol. Biol.*, 128, 577–594 (1973); Steenberg et al., *Nucleic Acids Res.*, 4, 4371–4389 (1977); Tooze, *DNA Tumor Viruses* (2nd ed., Cold Spring Harbor, N.Y.: Cold Spring Harbor Laboratory, 1981), pp. 943–1054). The ITRs harbor origins of DNA replication (Garon et al., supra; Wolfson et al., supra; Arrand et al., supra; Steenberg et al., supra).

The viral DNA is associated with four polypeptides, namely V, VII, m, and terminal polypeptide (TP). The 55 kd TP is covalently linked to the 5' ends of the DNA via a dCMP (Rekosh et al., *Cell*, 11, 283–295 (1977); Robinson et al., *Virology*, 56, 54–69 (1973)). The other three polypeptides are noncovalently bound to the DNA and fold it in such a way as to fit it into the small volume of the capsid. The DNA appears to be packaged into a structure similar to cellular nucleosomes as seen from nuclease digestion patterns (Corden et al., *Proc. Natl. Acad. Sci. USA*, 73, 401–404 (1976); Tate et al., *Nucleic Acids Res.*, 6, 2769–2785 (1979); Mirza et al., *Biochim. Biophys. Acta*, 696, 76–86 (1982)).

Beyond the various physical similarities characteristic of the adenoviruses, these viruses have been distinguished into subdivisions with respect to certain criteria, including immunological reactivities, oncogenicity, and GC content of the genome of a given strain. See Horwitz, supra at 777. For example, over 40 serotypes and four hemagglutination groups have been identified among human adenovirus isolates. The following chart summarizes the classification of human adenoviruses, as reviewed by Horwitz, supra at 777:

| | | | Oncogenic potential | | |
|---|---|---|---|---|---|
| Subgroup | Hemagglutination groups | Seritypes | Tumors in animals | Transformation in tissue culture | Percentage of G + C in DNA |
| A | IV (little or no agglutination) | 12, 18, 31 | High | + | 48–49 |
| B | I (complete agglutination of monkey erythrocytes) | 3, 7, 11, 14, 16, 21, 34, 35 | Moderate | + | 50–52 |
| C | III (partial agglutination of rat erythrocytes) | 1, 2, 5, 6 | Low or none | + | 57–59 |
| D | II (complete agglutination of rat erythrocytes) | 8, 9, 19, 37, 10, 13, 15, 17, 19, 20, 22–30, 32, 33, 36, 37, 38, 39, 42 | Low or none | + | 57–61 |
| E | III | 4 | Low or none | + | 57–59 |
| F | III | 40, 41 | Unknown | | |

At least with respect to the adenoviral serotypes that have been most studied to date, namely Ad2 and Ad5, which have been fully sequenced, the overall organization of the adenoviral genome is conserved among serotypes such that specific functions are similarly positioned. Portions of other serotypes have been sequenced, the results of which are consistent with the hypothesis of a conserved genetic organization among the adenoviruses. Nevertheless, as is reflected in the chart, the adenoviruses exhibit substantial diversity at the genetic level. For example, viral isolates from the different groups of adenoviruses exhibit variant GC contents in their respective genomes. Moreover, DNA—DNA hybridization studies indicate that there is less than 20% homology between the DNA of different groups, although more refined analysis reveals that conserved sequences can be detected in comparisons of subgenomic segments. For example, in studies of up to 30 map units of DNA length, at least 20–50% of the DNA sequence is noted to vary between groups (Horwitz, supra at 777). In another study, sequences of the origin of replication of subtypes associated with each of the six groups of adenoviruses have been noted to be related but different.

Importantly, albeit unexplained, adenoviruses of different groups do not recombine when co-infection of the same host occurs. In contrast, the adenoviruses recombine efficiently within a group (Sambrook et al., *J. Mol. Biol.*, 97, 369–390 (1975)). The failure of adenoviruses to recombine between serogroups highlights the genetic variance of the adenoviral groups.

The basic physiology of adenoviral infection has been studied predominantly with respect to Ad2 and Ad5. According to those studies, adenovirus begins to infect a cell by attachment of the fiber to a specific receptor on the cell membrane (Londberg-Holm et al., *J. Virol.*, 4, 323–338 (1969); Morgan et al., *J. Virol.*, 4, 777–796 (1969); Pastan et al., "Adenovirus entry into cells: some new observations on an old problem," in *Concepts in Viral Pathogenesis*, Notkins et al., eds., Springer-Verlag, New York, N.Y., pp. 141–146 (1987)). Then, the penton base binds to a cellular integrin receptor. The receptor-bound virus then migrates from the plasma membrane to clathrin-coated pits that form endocytic vesicles or receptosomes, where the pH drops to 5.5. The drop in pH is believed to alter the surface configuration of the virus, resulting in receptosome rupture and release of virus into the cytoplasm of the cell.

When the virus reaches the nuclear pores, the viral DNA enters the nucleus, leaving most of the remaining protein behind in the cytoplasm (Philipson et al., *J. Virol.*, 2, 1064–1075 (1968)). However, the viral DNA is not completely protein-free in that at least a portion of the viral DNA is associated with at least four viral polypeptides, namely V, VII, TP and m, and is converted into a viral DNA-cell histone complex (Tate et al., *Nucleic Acids Res.*, 6, 2769–2785 (1979)).

The cycle from cell infection to production of viral particles lasts 1–2 days and results in the production of up to 10,000 infectious particles per cell (Green et al., *Virology*, 13, 169–176 (1961)). The infection process of adenovirus is divided into early (E) and late (L) phases, which are separated by viral DNA replication, although some events that take place during the early phase also take place during the late phase and vice versa. Further subdivisions of the adenoviral genetic regions have been made to fully describe the temporal expression of viral genes.

During the early phase, viral messenger RNA ("mRNA"), which constitutes a minor proportion of the total RNA present in the cell, is synthesized from both strands of the adenoviral DNA present in the cell nucleus. At least five regions, designated E1, E2, E3, E4, and MLP-L1, are transcribed (Lewis et al., *Cell*, 7, 141–151 (1976); Sharp et al., *Virology*, 75, 442–456 (1976); Sharp, "Adenovirus transcription," in *The Adenoviruses*, Ginsberg, ed., Plenum Press, New York, N.Y., pp. 173–204 (1984)). Each region has at least one distinct promoter and is processed to generate multiple mRNA species.

The products of the early (E) regions (1) serve regulatory roles for the expression of other viral components, (2) are involved in the general shut-off of cellular DNA replication and protein synthesis, and (3) are required for viral DNA replication. The intricate series of events regulating early mRNA transcription begins with expression of certain immediate early regions, including E1A, L1, and the 13.5 kd gene (reviewed in Sharp (1984), supra; Horwitz, supra). Expression of the delayed early regions E1B, E2A, E2B, E3 and E4 is dependent on the E1A gene products. Three promoters—the E2 promoter at 72 map units ("mu"), the protein IX promoter, and the IVa promoter—are enhanced by the onset of DNA replication, but are not dependent on it (Wilson et al., *Virology*, 94, 175–184 (1979)). Their expression characterizes an intermediate phase of viral gene expression. The result of the cascade of early gene expression is the start of viral DNA replication.

Adenoviral DNA replication displaces one parental single-strand by continuous synthesis in the 5' to 3' direction from replication origins at either end of the genome (reviewed in Kelly et al., "Initiation of viral DNA replication," in *Advances in Virus Research*, Maramorosch et al., eds., Academic Press, Inc., San Diego, Calif. 34, 1–42 (1988); Horwitz et al., in *Virology*, Raven Press, New York, 2, 1679–1721 (1990); van der Vliet, "Adenovirus DNA replication in vitro," in *The Eukaryotic Nucleus*, Strauss et al., eds., Telford Press, Caldwell, N.J., 1, 1–29 (1990)). Three viral proteins encoded from E2 are essential for adenoviral DNA synthesis: (1) the single-stranded DNA binding protein (DBP), (2) the adenoviral DNA polymerase (Ad pol), and (3) the pre-terminal protein (pTP). In addition to these essential proteins, in vitro experiments have identified many host cell factors necessary for DNA synthesis.

DNA synthesis is initiated by the covalent attachment of a dCMP molecule to a serine residue of pTP. The pTP-DCMP complex then functions as the primer for Ad pol to elongate. The displaced parental single-strand can form a panhandle structure by base-pairing of the inverted terminal repeats. This terminal duplex structure is identical to the ends of the parental genome and can serve as an origin for the initiation of complementary strand synthesis. Initiation of viral DNA replication appears to be essential for entry into the late phase. The late phase of viral infection is characterized by the production of large amounts of the viral structural polypeptides and the nonstructural proteins involved in capsid assembly. The major late promoter (MLP) becomes fully active and produces transcripts that originate at 16.5 mu and terminate near the end of the genome. Post-transcriptional processing of this long transcript gives rise to five families of late mRNA, designated respectively as L1 to L5 (Shaw et al., *Cell*, 22, 905–916 (1980)). The mechanisms that control the shift from the early to late phase and result in such a dramatic shift in transcriptional utilization are unclear. The requirement for DNA replication may be a cis-property of the DNA template, because late transcription does not occur from a superinfecting virus at a time when late transcription of the primary infecting virus is active (Thomas et al., *Cell*, 22, 523–533 (1980)).

Assembly of the virion is an intricate process from the first step of assembling major structural units from individual polypeptide chains (reviewed in Philipson, "Adenovirus Assembly," in *The Adenoviruses*, Ginsberg, ed., Plenum Press, New York, N.Y. (1984), pp. 309–337; Horwitz, supra). Hexon, penton base, and fiber assemble into trimeric homopolymer forms after synthesis in the cytoplasm. The 100 kd protein appears to function as a scaffolding protein for hexon trimerization, and the resulting hexon trimer is called a hexon capsomer. The hexon capsomeres can self-assemble to form the shell of an empty capsid, and the penton base and fiber trimers can combine to form the penton when the components are inside the nucleus. The facet of the icosahedron is made up of three hexon capsomeres, which can be seen by dissociation of the capsid, but the intermediate step of the formation of a group-of-nine hexons has not been observed. Several assembly intermediates have been shown from experiments with temperature-sensitive mutants. The progression of capsid assembly appears dependent on scaffolding proteins, 50 kd and 30 kd. The naked DNA most probably enters the near-completed capsid through an opening at one of the vertices. The last step of the process involves the proteolytic trimming of the precursor polypeptides pVI, pVII, pVIII and pTP, which stabilizes the capsid structure, renders the DNA insensitive to nuclease treatment, and yields a mature virion.

Replication deficient adenoviruses are known to have a variety of uses. For example, replication deficient adenovirus are useful for transfer of genes and other genetic elements, such as ribozymes, antisense RNAs and DNA segments that express the like, to cells in vivo and in vitro. In vivo uses also include genetically altering cells for diagnostic or therapeutic purposes, and the study of biological phenomena, such as elements governing protein half-life, transcription rates, and protein function. In vitro uses also include the study of the biological phenomena listed above, and can be advantageous in that experimental conditions can be more precisely controlled.

Certain recombinant adenoviral vectors have been used in gene therapy, namely Ad2 and Ad5, both of which are members of group C. The use of a recombinant adenoviral vector to transfer one or more recombinant genes enables targeted delivery of the gene or genes to an organ, tissue, or cells in need of treatment, thereby overcoming the delivery problem encountered in most forms of somatic gene therapy. Furthermore, recombinant adenoviral vectors do not require host cell proliferation for expression of adenoviral proteins (Horwitz et al., supra; Berkner, *BioTechniques*, 6, 616 (1988)). Moreover, if the diseased organ in need of treatment is the lung, use of adenovirus as the vector of genetic information has the added advantage of adenovirus being normally trophic for the =respiratory epithelium (Straus, in *Adenoviruses*, Plenum Press, New York, pp. 451–496 (1984)).

Other advantages of adenoviruses as vectors for human gene therapy include: (i) recombination is rare; (ii) the adenoviral genome (which is linear, double-stranded DNA) currently can be manipulated to accommodate foreign genes ranging in size of at least 7.5 kb in length; (iii) an adenoviral vector does not insert its DNA into the chromosome of a cell, so its effect is impermanent and unlikely to interfere with the cell's normal function; (iv) the adenovirus can infect non-dividing or terminally differentiated cells, such as cells in the brain and lungs; and (v) live adenovirus, having as an essential characteristic the ability to replicate, has been safely used as a human vaccine (Horwitz et al., supra; Berkner et al., *J. Virol.*, 61, 1213–1220 (1987); Straus supra; Chanock et al., JAMA, 195, 151 (1966); Haj-Ahmad et al., *J. Virol.*, 57, 267 (1986); Ballay et al., *EMBO*, 4, 3861 (1985)).

Foreign genes have been inserted into various major regions of the group C adenoviral genome for use as expression vectors, most commonly the E1, E3, and E4 regions, thus providing singly deficient adenovirus and vectors derived therefrom. Insertion into the E1 region of an adenovirus results in defective progeny that require either growth in complementary cells or the presence of a helper virus, either of which provides in trans the function of the impaired or absent E1 region (Berkner et al., supra; Davidson et al., *J. Virol.*, 61, 1226–1239 (1987); Mansour et al., *Mol. Cell Biol.*, 6, 2684–2694 (1986)). Examples of cell lines that complement for deficiencies of essential adenoviral gene functions include the human embryonic kidney cells known as HEK-293 (Graham et al., *Cold Spring Harbor Symp. Quant. Biol.*, 39, 637–650 (1975)), W162 (Weinberg et al., *Proc. Natl. Acad. Sci. USA*, 80, 5383–5386 (1983)), gMDBP (Klessig et al., *Mol. Cell. Biol.*, 4, 1354–1362 (1984); Brough et al., *Virology*, 190, 624–634 (1992)) and 293/ORF6 cells (WO 95/34671, Kovesdi et al.).

The E1 region of the genome has been used most frequently for expression of foreign nucleic acid. Genes inserted into the E1 region have been placed under the control of various promoters, and most produce large amounts of the foreign gene product, dependent on the expression cassette.

The E3 region is not essential for virus growth in tissue culture, and the replacement of this region with a foreign nucleic acid expression cassette leads to a virus that can productively grow in a noncomplementing cell line. For example, the insertion and expression of the hepatitis B surface antigen in the E3 region of serotype Ad5 virus with subsequent inoculation and formation of antibodies in the hamster has been reported (Morin et al., *Proc. Natl. Acad. Sci. USA*, 84, 4626–4630 (1987)). Reports of analogous E3 deficiencies created in Ad4 and Ad7 serotypes have also been reported (regarding Ad4, Chengalvala et al., *Vaccine*, 9, 485–490 (1991); regarding Ad7, Lindley et al., *Gene*, 138, 165–170 (1994) and Chengalvala et al., *J. Gen. Virol.*, 75, 125–131 (1994)).

In the field of adenoviral gene therapy, clinical studies to date have used only the two aforementioned group C serotypes, namely Ad2 and Ad5. As examples of such studies, see Davidson et al., *Nature*, 3, 219 (1993), and Mastrangeli et al., *J. Clin. Invest.*, 91, 225–234 (1993). The focus of current studies on the group C serotypes can be understood in view of the fact that the overwhelming majority of basic research studies of characterization of the adenoviruses has been directed to Ad2 and Ad5. See Fields, supra; see also, *The Adenoviruses* (Ginsberg, ed., Plenum Press, New York, N.Y., 1984). These studies have shown that the group C adenoviruses are exceptionally effective as delivery vehicles for a variety of target tissues, including the respiratory epithelium. See, e.g., Bajocchi et al., *Nature Genetics*, 3, 229–234 (1993).

There are, however, limitations on the use of group C adenoviral gene therapy vectors. A host can develop an immune response to the particular adenoviral vector being used in gene therapy as a result of natural exposure of the host to the same type of adenovirus prior to the initiation of gene therapy or as a result of the exposure of the host to the adenoviral vector in the course of the gene therapy itself. A cellular immune response can reduce the life span of cells infected with the adenoviral vector and thereby reduce the expression of the foreign nucleic acid and diminish the overall effectiveness of the gene therapy. Indeed, it has been noted empirically that a major limitation of the currently used group C adenoviral gene therapy systems is the short duration of gene expression obtained thereby. See, e.g., Crystal et al., *Nature Genetics*, 8, 42–51 (1994). Moreover, a humoral immune response, resulting in the production of antibodies, can significantly reduce the effectiveness of gene therapy using a particular adenoviral vector. Obviously, this neutralization of the adenovirus impairs gene therapy and the in vivo use of adenoviral vectors for biological research applications.

For many of these applications it is useful to use a replication deficient adenovirus of a particular serotype. The reasons for this are multifold, but include the fact one serotype of adenovirus by definition is not reactive to an adenovirus of another serotype. Therefore, if a mammal, including a human, is exposed to one serotype of adenovirus, it will develop an immune reaction specific for that strain of adenovirus, but not to distinct strains. Thus, distinct strains can then be used to avoid the humoral and the cellular immune responses specific for other adenoviruses. Moreover, different serotypes of adenoviruses are trophic for distinct cell types. Thus, a replication deficient adenovirus useful in transferring passenger genes to one cell type can be less optimal than a second adenovirus for transfer of that passenger gene to a second cell type. Thus, there is a need for replication deficient adenoviruses of multiple strains. However, if each adenoviral strain requires its own complementing cell, even if that complementing cell were constructed by co-infection with a helper virus, it would be an expensive, tedious, and time consuming process to produce a new complementing cell line for each adenoviral serotype.

Accordingly, a method of producing non-group C adenoviral vectors was devised and is the subject of U.S. patent application Ser. No. 08/537,402. The '402 application disclosed that surprisingly complementary cell lines, such as HEK-293, which were produced or can be produced to complement replication-deficiencies in group C vectors can be used to complement the production of non-group C adenoviral vectors. However, the use of such group C complementing cell lines to complement the growth of non-group C vectors results in weak complementation. Unfortunately, this weak complementation makes it difficult to recover pure stocks (i.e., not contaminated by wild-type virus) of E1-deficient adenoviral vectors of a non-group C serotype, especially when the use of homologous recombination of an isolated arm of the virus is used to prepare E1-deficient non-group C vectors.

Additionally, production of group C adenoviral vectors in complementing cell lines developed for non-group C adenoviruses is useful, because, inter alia, recombination between the genome of the complementing cell line and the group C adenovirus is highly disfavored.

Accordingly, there is a need for an improved method of producing E1-deficient adenoviral vectors, especially wherein the deficiency in E1 results in a replication deficiency. The present invention seeks to provide such vectors and methods of producing such vectors. These and other objects and advantages of the present invention, as well as additional inventive features, will be apparent from the description of the present invention herein.

BRIEF SUMMARY OF THE INVENTION

The present invention provides a method of producing a replication deficient adenovirus comprising a passenger gene and a deficiency in an essential gene function of the E1 region of an adenovirus, in which the method comprises producing the adenovirus in a cell that provides in trans gene functions of the E1 and E4 regions of one or more adenoviruses not belonging to the same serogroup as the replication deficient adenovirus. The present invention also provides the adenoviruses produced in accordance with the present invention.

DETAILED DESCRIPTION OF THE INVENTION

The present invention provides a method of producing a replication deficient adenovirus that is deficient in the E1 region of the adenoviral genome comprising a passenger gene that obviates the need for separate complementing cells for each adenoviral strain.

E1 deficient group C adenoviruses effectively grow in cells that provide in trans the deficient essential gene product, when the essential gene product is derived from an adenovirus of the same or of a similar serotype (e.g., E1 deficient Ad2 and Ad5 grow well in 293 cells). Additionally, cells that efficiently complement for essential gene function defects of one particular serotype of adenovirus are not necessarily efficient for complementation of the growth of replication deficient adenoviruses of other serotypes. For example, an E1 deficient Ad5 (of serogroup C) grows substantially better in 293 cells than a homologous E1 deficient Ad7 (of serogroup B). While not wishing to be bound by any particular theory, it is believed that because the E1 gene products in 293 cells were derived from a group C adenovirus, 293 cells are able to more fully complement the growth of group C adenoviruses compared to other adenoviruses.

In the present inventive method, a replication deficient adenovirus having a genome deficient in an essential gene function of the E1 region of the adenoviral genome (or DNA segments comprising the genome of a replication deficient adenovirus) is transferred to a complementing cell. If the genome is carried on more than one DNA segment, or in a discontinuous fashion, homologous recombination or DNA ligation occurs within the cell to produce a replication deficient adenoviral genome. Alternatively, a replication deficient adenovirus can be infected into the cell or its DNA can be inserted into the cell by any suitable transfection technique known in the field (e.g., electroporation). The complementing cell provides in trans: one or more essential gene functions of the E1 region of an adenoviral genome, and one or more gene functions of the E4 region of an adenoviral genome. Surprisingly, this provision in trans of both E1 and E4 functions in the cell, rather than only E1 functions, allows enhanced production of replication deficient adenovirus when the serotype of the adenovirus from which the essential E1 product provided in trans is derived, and the serotype of the replication deficient adenovirus belong to different serogroups. The cell comprising the replication deficient adenovirus genome is then maintained in culture for a sufficient period of time to generate replication deficient adenovirus. The replication deficient adenovirus can be harvested by any suitable method to provide a stock of the replication deficient adenovirus.

While not wishing to be bound by any particular theory. However, applicant believes that the E4 gene product and the essential E1 gene product functionally interact to more fully complement the adenovirus. The ability to functionally interact appears to be absolutely conserved within a serotype, but less conserved between differing serotypes of a serogroup, and nonconserved between viruses of differing serogroups. Thus, it will be readily appreciated that in some embodiments of the present invention it is preferable for the essential gene products of the E1 and E4 regions of the adenoviral genome to be derived from the same serogroup, and even more preferable for them to be derived from the same serotype.

The E4 region contains only one essential gene function but this gene function is at least partially redundant within the E4 region of the adenoviral genome. That is, while the E4/ORF6 gene function is often referred to as the essential gene function of the E4 region of the adenoviral genome, that view may be oversimplified in some respects. For example, the E4/ORF3 gene function can partially substitute for the E4/ORF6 gene product. Additionally, the E4/ORF6/7 has occasionally been defined as the E4 essential gene function. However, complementation and other studies have demonstrated that the single gene function of the E4 region which is necessary and optimally complements for deletion of the entire E4 region is ORF6. Accordingly, the essential gene function of the E4 region of the adenoviral genome that is provided in trans is preferably the E4/ORF6 gene function for many embodiments of the present invention.

While not wishing to be bound by any particular theory, it is believed that the ORF6 gene product interacts preferentially with the gene product of the E1B region of the adenoviral genome. Accordingly, the essential gene function of the E1 region of the adenoviral genome that is provided in trans is preferably the E1B gene function for many embodiments of the present invention.

The E1B gene product is also known to interact with the non-essential gene product of E4/ORF4. Thus, the present invention also contemplates that the E4 gene product provided in trans by the complementing cell is the E4/ORF4 gene product.

It is often useful to establish a cell line which provides the gene functions of the E1 and E4 regions from DNA which is stably incorporated in the cell, especially in the genome of the cell. Such cell lines obviate the need to create a complementing cell line each time the skilled artisan desires to make a replication deficient adenovirus. Alternatively, either the gene function of the E1 or the E4 region can be stably incorporated in the cell, which would then require the transient provision of the other gene function. This is most easily illustrated in the well known HEK-293 cell line which already contains the essential gene functions of the E1 region. By way of example, a helping virus expressing E4/ORF6 in a 293 cell will suitably give rise to a complementary cell. Alternatively, a 293/ORF6 cell line can be used as the complementing cell line useful in the context of the present invention. The technology for the production of a 293/ORF6 cell and other cells that stably incorporate and express DNA capable of providing both E1 and E4 essential gene functions is well known in the art, and described, for example, in International Patent Application WO 95/34671 (Kovesdi et al.).

WO 95/34671 discloses that complementary cell lines for replication deficient adenoviruses lacking the E1 and E4 regions of the adenoviral genome can be produced by incorporating DNA segments encoding the essential gene products into the genome of the cell line. These DNA segments are operably linked to promoters which direct the expression of sufficient levels of the gene product(s) to enable the replication of the replication deficient (E1$^-$, E4$^-$) adenovirus. WO 95/34671 also teaches that the essential gene functions of the E4 region are harmful to the host cell. Therefore, it is useful to use a regulable promoter so that the gene function of the E4 region can be provided only when the replication deficient adenovirus is in need of the toxic gene products for its replication. Similarly, the essential gene functions of the E1 region affect a host cell's characteristics. Therefore, it can also be useful to place the E1 gene functions under the control of a regulable promoter.

Whereas there are certain clear advantages of stably incorporating the E1 and E4 gene functions into the complementing cell, there are also appealing reasons to provide these functions in a transient fashion. For example, at least one essential gene function of the E1 region and one gene function of the E4 region of an adenoviral genome can be provided in trans by a helper virus that produces these gene functions when it infects a cell. Similarly, a complementing cell can be created by transfection of a host cell with plasmids or other DNA moieties. Preferably, in this or any embodiment, a highly efficient method of transfection or infection is employed, or, alternatively, transfected cells are placed under selective pressure, e.g., by use of antibiotics with a plasmid that carries an antibiotic resistance gene. Significant advantages of transiently providing the DNA(s) encoding the complementing gene functions include, but are not limited to, not having to maintain a cell line and a relatively rapid development of a complementing cell.

In accordance with the description above, the DNA comprising the replication deficient adenoviral genome can be transferred to the complementing cell by infection. This method of delivery to the complementing cell of DNA comprising the adenoviral genome is particularly useful if a particular adenoviral stock comprises both the desired replication deficient adenovirus and another type of adenovirus. In this instance, the desired replication deficient adenovirus of a first serotype can be more easily plaque purified because when the complementing cell provides both essential region E1 and essential region E4 gene products of a second (or second and third) serotype, the particle to pfu ratio drops substantially, by about 3 to 5 fold. This drop in the particle to pfu ratio (for the replication deficient adenovirus) means that a contaminating virus (i.e., not the desired replication deficient adenovirus) is significantly less likely to be present in any given plaque. Moreover, the drop in particle to pfu ratio indicates that the level of complementation of the deficiency of the replication deficient adenovirus is increased. Thus, any potential growth advantage of a contaminating adenovirus would be decreased. Therefore, the present invention provides an improved method of plaque purifying a replication deficient adenovirus produced in a complementing cell line expressing a complementing essential gene function of an adenovirus belonging to a different serogroup.

Another method of transferring the DNA comprising the replication deficient adenoviral genome to the complementing cell is by transfection. This embodiment of the inventive method encompasses transfection wherein the adenoviral genome is provided on at least two separate DNA segments. In this embodiment, the replication deficient adenoviral genome can be created, propagated, and packaged in one step.

Multiple cell lines that complement for deficiencies in essential gene functions of Ad2 or Ad5, which are group C adenoviruses, have been previously developed. These cell lines especially include those that complement for deficiencies of essential E1 gene functions, such as HEK-293 cells and 293/ORF6 cells. In the context of the present invention, these cell lines, particularly those that complement for the essential E1A gene function allow for the creation of a replication deficient adenovirus that is reactive with antibodies specific for a group A, B, D, E, or F adenovirus, but not necessarily with antibodies that are able to neutralize an infection of a group C adenovirus, in a cell line that has already been established for the propagation of group C adenoviruses. By neutralize is meant the ability of an antibody which is bound in stochiometric levels to a virus (i.e., 1 antibody to 1 virus particle) to prevent the infection of a suitable host cell for that virus. This replication deficient adenovirus is characterized by the incorporation of an adenoviral DNA segment isolated from an adenovirus or substantially homologous to a DNA segment contained in an adenovirus. Optionally, of course, the adenovirus can also carry a passenger gene.

While the adenoviral DNA segment which forms part of the present inventive adenoviral vector is preferably isolated from an adenovirus, the adenoviral DNA segment also can be substantially homologous to a DNA segment contained in such an adenovirus. The term "substantially homologous" as used herein refers to the ability of two nucleic acids to hybridize under at least moderately stringent hybridization conditions. Stringency of hybridization is a term of art that refers to the conditions used for a hybridization reaction whereby complementary single strands of nucleic acid join to one another to form double-stranded nucleic acid with some degree of mismatch, the degree of which is a function of the stringency used. In particular, the stringency will depend upon the size and composition of the strands of nucleic acid that are caused to react, the degree of mismatching allowed, the desired cross reactivity, and the like. The degree of stringency can be affected by the ionic conditions employed and temperature, among others, as is well known in the art (Sambrook et al., *Molecular Cloning: A Laboratory Manual* (2d ed., 1989)).

As used in the context of the present invention, the specified stringency of hybridization in part defines the inventive DNA segment. Accordingly, the hybridization conditions are designed suitably to be at least moderately stringent or stringent. In the former case, suitable conditions of salt, temperature, reaction mixture, and size of nucleic acid reactants are set in accordance with conventional knowledge to provide from about 45% to about 80% mismatch of the sequence of nucleotides of the nucleic acid. Preferably, moderately stringent hybridization conditions are set to provide from about 55% to about 75% mismatch; more preferably, such conditions are set to provide from about 60% to about 70% mismatch. In the latter case, suitable conditions for hybridization are set in accordance with conventional knowledge to provide from about 10% to about 40% mismatch. Preferably, stringent hybridization conditions are set to provide from about 20% to about 40% mismatch; more preferably, such conditions are set to provide from about 30% to about 40% mismatch. By mismatch, it is meant the degree to which non-complementary base pairs are found opposite one another in otherwise duplex DNA, thereby forming bubble structures and causing the melting temperature of the duplex to be lower as compared to a 100% matched duplex of the same length and base composition.

The present inventive adenoviral vector preferably further comprises a passenger gene, which will typically encode, and express within a host cell, a product that has investigational (such as marker genes), therapeutic, and/or prophylactic utility. Such a passenger gene encodes RNA, antisense RNA, a synthetic oligonucleotide, and/or a polypeptide. Passenger genes having therapeutic utility include genes that encode a missing or impaired gene function, such as the cystic fibrosis transmembrane regulator (CFTR) gene associated with cystic fibrosis (CF). Foreign nucleic acids having prophylactic utility include genes that encode a gene product that has an ability to prevent disease directly or indirectly, such as by providing a source of a polypeptide or other antigen to elicit an immune response thereto.

The present invention is illustrated by the following examples, which should not be construed as in any way limiting the scope of the present invention.

EXAMPLE 1

This example illustrates the deletion of the E1A region from the adenoviral DNA of Ad7a virus of group B, thereby generating viral large fragments.

Ad7a virus was used to inoculate HEK-293 cells in modified Eagle's medium with 5% horse serum at 100 multiplicity of infection, and the DNA was isolated from harvested Ad7a virus, using the methods described in Falck-Pedersen, in *Cell Biology: A Laboratory Manual* (Spector et al., eds., Cold Spring Harbor Laboratory, New York, 1994). Ad7a DNA was then subjected to restriction endonuclease cleavage with Aat II according to Dijkema et al., *Gene*, 12, 287 (1980), thereby producing a 1.483 kb small fragment (fragment 1) of the left hand, a large fragment of approximately 30 kb located in the center of the genome (fragment 2), and a second large fragment of 5 kb of the right hand (fragment 3). The small fragment includes the origin of replication and packaging sequences as well as early region E1A, which is necessary for DNA replication. The large fragments contain the other early genes as well as the late genes required for production of new virions.

Large fragments 2 and 3 were copurified and isolated separately from the small fragment by sucrose density gradient centrifugation. A 10% to 20% continuous sucrose gradient with a 40% sucrose cushion was overlayed with Aat II digested Ad7a DNA. Following centrifugation, the gradient was fractionated. Fractions containing purified large fragments were analyzed by agarose gel electrophoresis and visualized by ethidium bromide staining.

Fractions containing the large fragments that were free of small fragments were pooled and concentrated by precipitation and subsequent reconstitution in a smaller volume. The pooled DNA segments were used in subsequent steps in the preparation of the Ad7a replication-deficient virus because of the presence of the large fragments (2 and 3) and the absence of the small fragment (1), which were known to include region E1A.

EXAMPLE 2

This example describes the generation of the plasmid pAd7aCMV-CATgD. The plasmid pAd7aCMV-CATgD was prepared by directional cloning in three sequential steps.

First, using the polymerase chain reaction (PCR), up to 475 base pairs of the left end of the Ad7a genome (located between 0 and 1.3 map units (mu) on the Ad7a genome) were amplified and isolated. The primers used for amplification contained a Sac I site (left end primer) and a Not I site (right end primer). The amplified DNA contained the essential origin (ori) and packaging sequences (pkg). The early regions E1A and a portion of E1B, located between 1.3 and 7.7 mu, were not amplified. A cloning vector, pBS (Stratagene Cloning Systems, La Jolla, Calif., was then opened with SacI-NotI, and the PCR fragment SacI-ori/pkg-NotI was inserted therein.

Second, using standard methods, the pBS vector was opened with NotI-SalI, and the cytomegalovirus promoter (CMV) was ligated to the ori and pkg elements, followed by the bacterial chloramphenicol acetyl transferase sequence (CAT) and the mouse B-maj globin poly (A) site.

Third, a region of 2.8 to 4.0 kb for overlap recombination with the Ad7a genome was generated by a first and second PCR primer. The first primer contained an NheI site, abutted to a SalI site, abutted to the sequence of Ad7a from and including position 2880 to and including 2816. The second primer contained an ApaI site, abutted to a KpnI site, abutted to the sequence of Ad7a from and including position 4000 to and including position 3986.

This overlap recombination fragment is located at 7.7 to 11.1 mu on the Ad7a genome. The pBS vector was then opened with SalI-KpnI, and the PCR fragment SalI-Ad7 overlap DNA 2.8–4.0 kb-KpnI was inserted therein, i.e., ligated to the aforementioned DNA construct after the poly (A) site, thus resulting in the generation of the pAd7aCMV-CATgD plasmid.

EXAMPLE 3

This example describes the generation of recombinant Ad7-CAT adenovirus and demonstrates the ability of the recombinant Ad7a adenovirus to be replicated in and complemented by HEK-293 cells.

Various ratios of micrograms of viral large fragments prepared in accordance with Example 1 and plasmid pAd7aCMV-CATgD prepared in accordance with Example 2 were transfected onto monolayers of HEK-293 cells ($10^6$ cells per 60 mm dish) by calcium phosphate precipitation. After one week, the cells were harvested, and a virus lysate was generated by repeat freeze-thaw cycles. A 10% portion of the resulting lysate (0.5 ml) was used to infect a fresh monolayer of HEK-293 cells. After 24 hours, these cells were harvested and lysates prepared. The lysates were tested for reporter gene activity, i.e., chloramphenicol acetyl transferase (CAT) activity, using the method disclosed in Gorman et al., *Mol. Cell Biol.*, 2, 1044–1051 (1982), and Gorman et al., *PNAS*, 79, 6777–6781 (1982). The resultant viral constructs were screened for their ability to induce CAT activity. Under conditions where no CAT activity was observed in the Gorman et al. assay (e.g., transfections involving no exogenous CAT cDNA), some constructs showed up to 50% acetylation of the chloramphenicol, demonstrating that the viral construct had been successfully made.

EXAMPLE 4

This example further confirms the generation of recombinant Ad7-CAT adenovirus and the ability of the recombinant Ad7 adenovirus to be replicated in and complemented by HEK-293 cells. In particular, this example describes the test of a secondary virus lysate for CAT gene expression.

A 1.0 ml aliquot of the primary lysate generated in accordance with Example 3 was used to infect a 60 mm dish of HEK-293 cells. After incubation for one week, the cells were harvested, and lysates were generated, as in Example 3. A 10% portion of each lysate was then used to infect a fresh monolayer of HEK-293 cells, and the resultant lysate thereof was tested for CAT activity.

The results of these CAT assays demonstrated that the transfection of 4.8 mg of large fragment combined with about an equal mass of circular plasmid results in strong CAT activity in a secondary lysate, which is the result of the viral activity of the progeny of the initially harvested recombinant virus particles.

Selected cell lysates were further characterized by infecting HEK-293 cells and harvesting viral DNA by a modified Hirt procedure (Falck-Pedersen, supra). Purified viral DNA was digested with Aat II in order to characterize the recombinant DNA. Control DNA was taken from wild-type Ad7a and wild-type Ad5 adenoviruses. Visual analysis of the restriction fragment sizes (separated by Agarose gel-electrophoresis) confirmed that the proper DNA constructs had been obtained.

EXAMPLE 5

A modified virus yield experiment in 293 and A549 cells was performed to characterize Ad7-CAT produced in accordance with the foregoing examples. The CAT activity of Ad7-CAT was compared to a homologous Ad5-CAT (derived from Ad5 and constructed in an identical fashion) in the 293 and A549 cells. When 293 cells were infected with 1 particle of Ad5-CAT, as expected, there was significant CAT activity in cellular lysates harvested 18 hours after infection. Also, as expected, the CAT activity increased in a Ad5-CAT dose dependent fashion. In contrast, Ad7-CAT did not produce any detectable CAT activity in 293 cells until the viral particle to cell ratio was increased to about 10:1. At a viral particle to cell ratio of 10:1, Ad5-CAT is about 35 times more effective at directing the production of CAT than Ad7-CAT. Additionally, the CAT activity produced by Ad7-CAT at a viral particle to cell ratio of 1000:1 is about the same as that obtained from Ad5-CAT at a viral particle to cell ratio of 10:1. Both Ad5-CAT and Ad7-CAT gave only low (two orders of magnitude less than Ad7-CAT in 293 cells) levels of CAT activity in A549 cells. This example shows that Ad7-CAT is inefficiently complemented by 293 cells, and is deficient in an essential gene function of the E1 region of the adenoviral genome.

EXAMPLE 6

This example demonstrates the increased efficiency of complementation of an E1 deficient non-group C adenovirus in 293/ORF6 cells compared to the efficiency of complementation in 293 cells.

Using standard plaquing protocols, the ability of wild type Ad7a virus to plaque on a variety of cell lines was established. However, the cytopathic effect of Ad7a and Ad5-based viruses are different during infection of either A549 cells or 293 cells. Additionally, plaque formation takes slightly longer for Ad7a compared to Ad5. Also, the particle to pfu ratios for Ad7a viruses (about 2000 particles/pfu or more) infecting 293 cells is considerably higher than the particle to pfu ratios of Ad5 infecting 293 cells (about 40–50 particles/pfu).

A mixture of Ad7-CAT and wild type Ad7a were plaqued on 293 cells. In several attempts, no plaques containing the E1 deficient Ad7 and not containing the wild type contaminating virus were identified. Repetitive plaquing merely increased the ratio of the wild type virus to E1 deficient virus.

The same plaquing procedure was then carried out using a modified 293 cell (which complements for E1A and E1B) and that expresses the ORF6 gene product of the E4 region of the adenoviral genome (i.e., 293/ORF6 cells). This procedure resulted in a significant increase in plaque number in comparison to the plaquing on normal 293 cells. Additionally, a visible improvement in plaque morphology was observed, suggesting a greater degree of complementation in the 293/ORF6 cells than in the 293 cells. Additionally, no E1A DNA was detected by PCR in the viral stocks (i.e., no contaminating wild type virus was found in the plaque purified stocks) and some of these replication competent adenovirus-free (RCA-free) Ad7-CAT stocks mediated the production of high levels of CAT in infected A549 cells. Additionally, a virus concentration of $10^{12}$ particles/ml was obtained without steps to increase the viral titer. The viral yield of about $2 \times 10^{12}$ viral particles from a confluent culture of 293/ORF6 cells in a 35 mm dish was essentially the same as that expected for Ad5 infections.

Thus, this example demonstrates that the provision of a gene function of the E4 region of the adenoviral genome in addition to the essential gene functions of the E1 region of the adenoviral genome surprisingly increases the efficiency of complementation of E1 deficient adenoviruses when the E1 gene products provided in trans are obtained from an adenovirus of a serogroup different from that of the replication deficient adenovirus.

EXAMPLE 7

This example sets forth the increased complementation of E1 deficiencies by the provision in trans of an E4 gene product other than ORF6. The production and degree of complementation of E1 deficient Ad7 is compared between 293 cells and 293/E4-ORF4 cells.

293/ORF4 cells are produced by incorporation into the genome of 293 cells of an ORF4 expression cassette. The ORF4 expression cassette contains either the sheep metallothionein promoter or the promoter of the LTR of MMTV operably linked to a DNA segment encoding the ORF4 gene product of Ad5. If the MMTV promoter is used, a second expression cassette is also incorporated into the cell which constitutively provides high levels of glucocorticoid receptor. Alternatively, an expression cassette for the essential gene functions of the E1 region of Ad5 and for the above described ORF4 expression cassette are incorporated into a second cell line, such as COS-1 cells, A549 cells, HeLa Cells, or 293 cells. The resultant cell line is called 293/ORF4.

A mixture of Ad7-CAT and wild type Ad7 are plaqued on 293/ORF4 to obtain individual plaques containing only E1 deficient Ad7.

EXAMPLE 8

This example evaluates the similarities between non-group C adenoviruses with respect to group C adenoviruses.

The similarities and differences between various adenovirus groups were examined by comparing the amino acid similarity and identity between the E1A and E1B gene products of Ad2 (group C), Ad5 (group C), Ad7 (group B), Ad12 (group A), and Ad40 (group F) adenoviruses. As regards viruses within the same group, specifically as between Ad2 and Ad5 within group C, there was 99% similarity and 98% identity between the E1A and E1B gene products of Ad2 and Ad5. In contrast, comparisons between the viruses of the different groups revealed a greatly reduced similarity and less identity. For example, there was 63–75% similarity and 40–53% identity between the E1A and E1B gene products of Ad7, Ad12, and Ad40 as compared with the E1A and E1B gene products of Ad2 and Ad5.

Significantly, however, particular domains were found to be conserved among the viruses of the different groups, e.g., as between the non-group C and group C adenovirus E1A and E1B gene products. Thus, the differences between particular non-group C viruses as compared to group C viruses were found to be similar, such that, for example, the demonstration of an ability of group B adenoviruses is indicative of the same ability being possessed by other non-group C adenoviruses. In particular, the demonstration of the ability of an E1-defective group B adenovirus, e.g., Ad7, to be complemented by HEK-293 cells (as demonstrated in Example 3) evidences the ability of other non-group C adenoviruses to be complemented by HEK-293 cells.

Any known serotype of adenovirus can be obtained and propagated by the skilled artisan. Having a stock of propagated virus, the skilled artisan can obtain the DNA from the virus and sequence it by any of a plethora of routine techniques, i.e., without doing anything out of the ordinary. It is then also straight-forward to identify the standard regions of the adenoviral genome by routine sequence comparison. Similarly, oligonucleotides can then be routinely designed and restriction enzyme sites routinely identified. Thus, while the methods employed in the examples herein demonstrate the use of Ad7, these methods are readily applicable to other adenoviral serotypes.

All references, including publications, patents, and patent applications, cited herein are hereby incorporated by reference to the same extent as if each reference were individually and specifically indicated to be incorporated by reference and were set forth in its entirety herein.

While this invention has been described with an emphasis upon preferred embodiments, it will be apparent to those of ordinary skill in the art that the preferred embodiments can be varied. Similarly, it is intended that the invention can be practiced otherwise than as specifically described herein. Accordingly, this invention includes all modifications encompassed within the spirit and scope of the appended claims.

What is claimed is:

1. A method of producing a replication deficient adenovirus comprising a passenger gene, said replication deficient adenovirus having a first serotype belonging to a first serogroup and having a genome deficient in an essential gene function of the E1 region of the adenoviral genome, said method comprising (a) transferring DNA comprising said adenoviral genome to a cell that provides in trans
      (i) one or more essential gene functions of the E1 region of an adenoviral genome derived from an adenoviral genome having a second serotype belonging to a second serogroup, and
      (ii) one or more gene functions of the E4 region of an adenoviral genome derived from an adenoviral genome having a third serotype belonging to said second serogroup, wherein the first serogroup is different than the second serogroup, (b) maintaining said cell to produce said replication deficient adenovirus.

2. The method of claim 1, wherein said first serogroup is selected from the group consisting of A, B, D, E, and F.

3. The method of claim 1, wherein said DNA comprising said adenoviral genome is transferred to said cell by transfection.

4. The method of claim 1, wherein said gene functions of the E1 and E4 regions of the adenoviral genome are of the same serotype.

5. The method of claim 4, wherein said gene functions of the E4 region of the adenoviral genome comprise the E4/ORF6 gene function.

6. The method of claim 5, wherein said cell provides a gene function of the E1B region of the adenoviral genome.

7. The method of claim 6, wherein at least one gene function of the E1 and E4 regions of an adenoviral genome provided in trans is expressed from DNA incorporated into the genome of said cell.

8. The method of claim 7, wherein all said gene functions of the E1 and E4 regions of an adenoviral genome provided in trans are expressed from DNA incorporated into the genome of said cell.

9. The method of claim 8, wherein said cell is a 293/ORF6 cell.

10. The method of claim 6, wherein at least one gene function of the E1 and E4 regions of an adenoviral genome provided in trans is expressed from DNA provided by a helper virus.

11. The method of claim 10, wherein all said gene functions of the E1 and E4 regions of an adenoviral genome provided in trans are expressed from DNA provided by a helper virus.

12. The method of claim 1, wherein said DNA comprising said adenoviral genome is transferred to said cell by infection.

13. The method of claim 12, wherein said cell is infected by a mixture of adenoviruses and wherein said replication deficient adenovirus is plaque purified.

14. The method of claim 3, wherein said DNA comprising said adenoviral genome is provided on at least two separate DNA segments.

* * * * *